(12) United States Patent
Gallenkamp et al.

(10) Patent No.: US 6,194,590 B1
(45) Date of Patent: Feb. 27, 2001

(54) METHOD FOR PREPARING OPTIONALLY SUBSTITUTED BENZOFURANONES

(75) Inventors: Bernd Gallenkamp, Wuppertal; Peter Gerdes, Aachen; Herbert Gayer, Monheim; Lothar Rohe, Wuppertal; Lubbertus Mulder, Hagen-Haspe, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/509,911

(22) PCT Filed: Sep. 30, 1998

(86) PCT No.: PCT/EP98/06213

§ 371 Date: Apr. 4, 2000

§ 102(e) Date: Apr. 4, 2000

(87) PCT Pub. No.: WO99/19316

PCT Pub. Date: Apr. 22, 1999

(30) Foreign Application Priority Data

Oct. 10, 1997 (DE) ............................................. 197 44 705

(51) Int. Cl.$^7$ .................................................. C07D 307/83

(52) U.S. Cl. .............................................................. 549/466
(58) Field of Search ............................................. 549/466

(56) References Cited

U.S. PATENT DOCUMENTS 5,679,679    10/1997    Bowen et al. ........................ 514/249

FOREIGN PATENT DOCUMENTS 196 02 095    7/1997    (DE) .

OTHER PUBLICATIONS

B. J. Chem. Soc. 99 pp. 911–916, 1911, Richard William Merriman, M.A. "Coumaranone Derivatives", Part 1.
Synthetic Communications, 1990, pp. 809–816, A. R. Deshpande and M. V. Paradkar, "Synthesis of 3–(3–Benzofuranyl)Coumarins".

*Primary Examiner*—Amelia Owens
(74) *Attorney, Agent, or Firm*—Joseph C. Gil

(57) ABSTRACT

The invention relates to an improved method for preparing optionally substituted benzofuran-3-ones which can be used as initial products for preparing 3-(1-hydroxyphenyl-1-alkoximinomethyl) dioxazines. These later are known starting materials for preparing compounds with fungicidal properties.

9 Claims, No Drawings

METHOD FOR PREPARING OPTIONALLY SUBSTITUTED BENZOFURANONES

This application is a 371 of PCT/EP98/06213 Sep. 30, 1998.

The invention relates to an improved process for the preparation of optionally substituted benzofuran-3-ones which can be employed as precursors for the preparation of 3-(1-hydroxyphenyl-1-alkoximinomethyl)dioxazines, which in turn are known as starting substances for the preparation of compounds having fungicidal properties (WO 95-04728 and DE-A-19602095).

It has already been disclosed that optionally substituted benzofuran-3-ones can be prepared in accordance with the following reaction scheme (J. Org. Chem. 1962, 586–591):

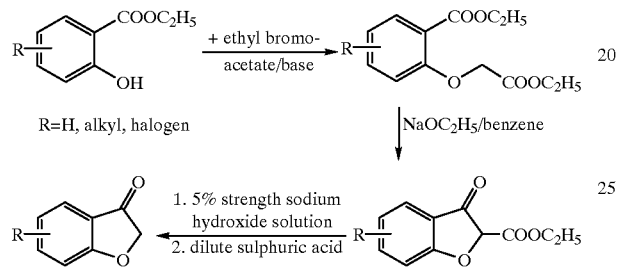

R=H, alkyl, halogen

A salicylic acid ethyl ester is first reacted with ethyl bromoacetate and the salicylic acid ether thus obtained is cyclized with sodium ethanolate in benzene to give a benzofuranonecarboxylic acid ethyl ester. This is hydrozysed in dilute sodium hydroxide solution and then decarboxylated with dilute sulphuric acid and the product is precipitated. The yields of this process are extremely unsatisfactory and the reaction times—the hydrolysis in particular lasts a week or more—are unacceptable for an industrial preparation.

An alternative synthesis for the preparation of optionally substituted benzofuranones is described in Synthetic Communications 1990, 809–816.

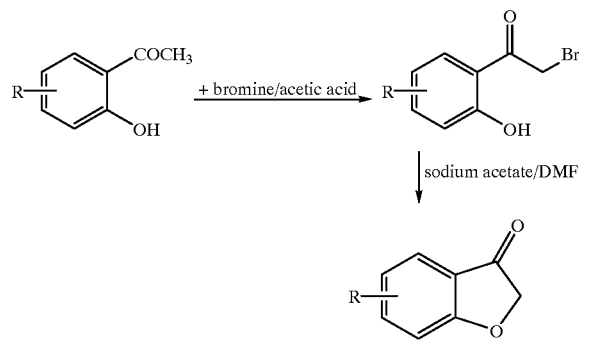

In this process, o-hydroxyacetophenone is first brominated with bromine in acetic acid and the brominated compound is cyclized with sodium acetate in dimethylformamide, hydrogen bromide being eliminated. In this process also, the yields are unsatisfactory. Furthermore, the bromine required as a reagent could be employed in an industrial synthesis only with a high expenditure on safety.

It has now been found that optionally substituted benzofuranones of the formula (I)

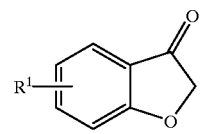

in which
$R^1$ represents hydrogen, alkyl or halogen,
are obtained in a high yield and high purity by a process in which salicylic acid ethers of the general formula (II)

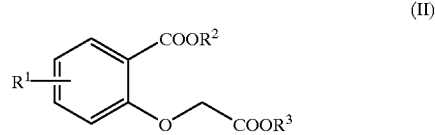

in which
$R^1$ has the abovementioned meaning and
$R^2$ and $R^3$ are identical or different and independently of one another represent alkyl,
are reacted in a first step with a strong base, preferably an alkali metal alcoholate, under an inert gas atmosphere, optionally in the presence of a diluent, and the benzofuranonecarboxylic acid ester obtained in this manner, of the formula (III)

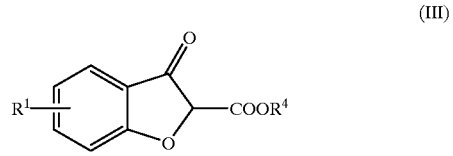

in which
$R^1$ has the abovementioned meaning and
$R^2$ represents alkyl,
is reacted in a second step first with potassium hydroxide, optionally in the presence of a diluent, and then with an acid to give the desired benzofuranones of the formula (I).

Benzofuranones of the formula (I) which can preferably be prepared are those in which
$R^1$ represents hydrogen, alkyl having 1 to 4 carbon atoms, fluorine or chlorine.

Benzofuranones of the formula (I) which can particularly preferably be prepared are those in which
$R^1$ represents hydrogen, methyl, ethyl, fluorine or chlorine.

Intermediate products of the formula (III) which can preferably be prepared are those benzofuranonecarboxylic acid esters of the formula (III) in which
$R^1$ represents hydrogen, alkyl having 1 to 4 carbon atoms, fluorine or chlorine and
$R^4$ represents alkyl having 1 to 4 carbon atoms.

Intermediate products of the formula (III) which can be particularly preferably prepared are those benzofuranonecarboxylic acid esters of the formula (III) in which
$R^1$ represents hydrogen, methyl, ethyl, fluorine or chlorine and
$R^4$ represents methyl or ethyl.

It is to be described as decidedly surprising that the first step of the process according to the invention tends towards less formation of by-products by working under the conditions according to the invention and thus gives substantially higher yields than the process known from the prior art. It is furthermore to be regarded as particularly surprising that the second step of the process according to the invention proceeds considerably faster and with considerably higher yields and purities by the use of the reaction conditions according to the invention than processes already described.

The process according to the invention is distinguished by a number of advantages. It thus allows the synthesis of benzofuranones of the formula (I) in a very high yield and purity. It is also favourable that the reaction components required are easy to prepare and are also available in relatively large amounts. Finally, another advantage is that carrying out the reaction and isolating the reaction products present no difficulties at all.

The general formula (II) provides a definition of the salicylic acid ethers required as starting substances for carrying out the first stage of the process according to the invention. In this formula (II), $R^1$ preferably or in particular has that meaning which has already been mentioned as preferred or as particularly preferred for $R^1$ in connection with the description of the compounds of the formula (I) which can be prepared according to the invention. $R^2$ and $R^3$ independently of one another represent alkyl, preferably having 1 to 4 carbon atoms, in particular ethyl or methyl.

The salicylic acid ethers of the formula (II) are known and/or can be prepared by known methods (compare, for example, B. J. Chem. Soc. 99 (1911), 911; and the preparation examples).

Possible diluents for carrying out the first stage of the process according to the invention are all the inert organic solvents. These include, preferably, aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; amides, such as N,N-dimethylformamide, N,N-dimethylacetamide, N-methylformanilide, N-methylpyrrolidone or hexamethylphosphoric acid triamide; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether and diethylene glycol monoethyl ether, and any desired mixtures of the diluents mentioned.

The first stage of the process according to the invention is carried out in the presence of a base. Preferred possible bases are alkaline earth metal or alkali metal hydrides or alcoholates, such as, for example, sodium hydride, sodium methylate, sodium ethylate or potassium tert-butylate.

The first stage of the process according to the invention is preferably carried out under an inert gas atmosphere. Possible inert gases are, for example, nitrogen or argon, and also solvent vapours.

The reaction temperatures can be varied within a relatively wide range when carrying out the first stage of the process according to the invention. In general, the reaction is carried out at temperatures from 0° C. to 150° C., preferably at temperatures from 0° C. to 80° C.

For carrying out the first stage of the process according to the invention for the preparation of the compounds of the formula (I), in general 0.5 to 10 mol, preferably 1 to 4 mol, of base are employed per mole of the salicylic acid ether of the formula (II).

When carrying out the first stage of the process according to the invention, the procedure is in general as follows: the salicylic acid ether of the formula (II) is dissolved or suspended in a diluent and the solution or suspension is then heated. The base, which is optionally predissolved in a diluent, is slowly added. After the end of the reaction, the mixture is worked up by customary methods. For example, the reaction mixture is introduced into water, the organic phase which may be present is separated off and discarded, the aqueous phase is acidified and the crystallized product is filtered off with suction and, if appropriate, dried.

While carrying out the entire reacton and during the working up, access of air or oxygen to the product is avoided. This is achieved either by working under an inert gas atmosphere, for example under nitrogen or argon, or carefully shielding the reaction mixtures from the outside air, for example by the solvent vapours lying on top. For example, by heating the solution of the starting substance of the formula (II) it is ensured that no air but only solvent vapour is directly above the surface of the solution. This reliably prevents the product formed after addition of the base from coming into contact with oxygen. Drying of the product, which may be desired, takes place in vacuo; the product is stored in a closed vessel under an inert gas atmosphere, for example under nitrogen or argon.

If an alcohol which differs from $R^3$—OH is used as the diluent or a diluent component or an alcoholate in which the alkyl group is other than $R^3$ is used as the base, partial or complete transesterification of the ester group of the benzofuranonecarboxylic acid ester formed, of the formula (III) also takes place, where appropriate, in addition to the desired cyclization. However, this is irrelevant for carrying out the second stage of the process according to the invention.

Possible diluents for carrying out the second stage of the process according to the invention are all the inert organic solvents. These include, preferably, ethers, such as diethyl ether, diisopropyl ether, methyl t-butyl ether, methyl t-butyl ether, dioxane, tetrahydrofuran, 1,2-dimethoxyethane, 1,2-diethoxyethane or anisole; amides, such as N,N-dimethylformamide, N,N-diemthylacetamide, N-methylformanilide, N-methylpyrrolidone or hexamethylphosphoric acid triamide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether and mixtures thereof with one another, and mixtures thereof with water or pure water.

An acid required for carrying out the second stage of the process according to the invention. Possible acids are all the inorganic and organic proton acids. Hydrochloric acid, sulphuric acid or phosphoric acid can preferably be used.

The second stage of the process according to the invention is preferably carried out under an inert gas atmosphere. Possible inert gases are, for example, nitrogen or argon.

The reaction temperatures can be varied within a relatively wide range when carrying out the second stage of the process according to the invention. The reaction is in general carried out at temperatures from 0° C. to 150° C., preferably at temperatures from 0° C. to 80° C.

For carrying out the second stage of the process according to the invention for the preparation of the compounds of the formula (I), in general 1 to 10 mol, preferably 2 to 8 mol of potassium hydroxide are employed per mole of the benzofuranonecarboxylic acid ester of the formula (III).

Both stages of the process according to the invention are in general carried out under normal pressure. However, it is also possible to carry out the process under increased or reduced pressure—in general under between 0.1 bar and 10 bar.

When carrying out the second stage of the process according to the invention, the procedure is in general as follows: the benzofuranonecarboxylic acid ester of the formula (II) obtained in the first stage of the process according to the invention is added to a potassium hydroxide solution and the reaction mixture is heated. After the end of the reaction, the reaction mixture is diluted, if appropriate, and an acid is then added, or, preferably, the reaction mixture is diluted, if appropriate, and then added dropwise to an acid. Working up is carried out by customary methods. For example, the product which precipitates out of the reaction mixture after cooling is filtered off with suction and, if appropriate, purified further, for example by steam distillation. While carrying out the entire reaction and during the working up, it is advantageous to avoid access of air or oxygen to the product.

Preparation examples:

Example 1

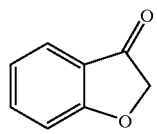

1st Stage:

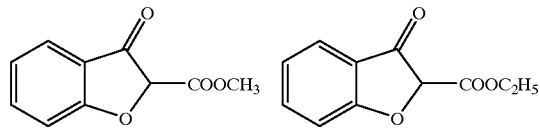

8200 g (32.25 mol) of methyl 2-ethoxycarbonylmethoxybenzoate are suspended in 26 l of toluene and the suspension is heated to 50° C. 6383 g (35.46 mol) of sodium methanolate solution (30% strength in methanol) are added dropwise at this temperature in the course of 15 minutes and the mixture is stirred at 50° C. for 2 hours. The reaction mixture is cooled at 20° C. and introduced into 82 l of ice-water, two phases forming. The organic phase is separated off and discarded. The aqueous phase is washed with 10 l of toluene, filtered and adjusted to a pH of 1–2 with concentrated hydrochloric acid at 15–20° C. The suspension formed here is diluted with 16 l of water, stirred and filtered with suction. The product is rinsed with 13 l of water in portions and stored in the damp state under a nitrogen atmosphere. 9500 g of water-moist product are obtained (5063.5 g=53.3% of dry substance). The dry substance contains 85.64% of methyl benzofuran-3-one-2-carboxylate (HPLC; logP=1.88) and 14.36% of ethyl benzofuran-3-one-2-carboxylate (HPLC; logP=2.32). The total yield is 84%. While carrying out the entire reaction and during the working up, ingress of air or oxygen to the product is avoided.

2nd Stage

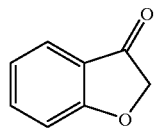

A solution is prepared from 8.2 l of water and 8262 g (125.4 mol) of potassium hydroxide (85% pure), 12.5 l of ethanol are added at 50–60° C. and 9079 g of the water-moist mixture, obtained in the 1st stage described above, of methyl benzofuran-3-one-2-carboxylate and ethyl benzofuran-3-one-2-carboxylate (24.79 mol in total) are then added. The mixture is heated under reflux for 45 minutes and 7.3 l of water are then added. This solution is cooled to 20° C. and introduced into a mixture, heated at 55° C., of 17.5 l of concentrated hydrochloric acid and 20 l water in the course of 60 minutes, vigorous evolution of gas taking place. Residues of the alkaline solution are rinsed out with 3 l of water and also introduced into the hydrochloric acid. The mixture is stirred at 60° C. for a further 30 minutes (end of the evolution of gas) and cooled to 20° C. The product is filtered off with suction, rinsed with 6 l of water and dried at 35° c. in a vacuum drying cabinet. 3250 g (94% of theory) of benzofuran-3-one are obtained. HPLC: logP=1.26.

Preparation of the starting substance:

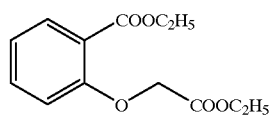

8020 g (65.44 mol) of ethyl chloroacetate are added to a mixture of 62 l of acetonitrile, 9490 g (62.38 mol) of methyl salicylate, 8610 g (62.38 mol) of potassium carbonate and 620 g of potassium iodide at 20° C., and the mixture is stirred and heated under reflux for 9 hours and stirred overnight without further heat being supplied. The mixture is filtered over Celite and the filtrate is concentrated under reduced pressure. 16.4 kg of methyl 2-ethoxycarbonylmethoxybenzoate are obtained (HPLC: logP=2.1)

Use example:

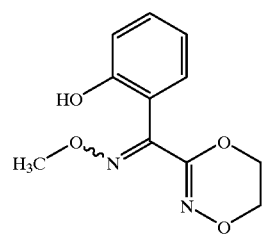

1st Stage:

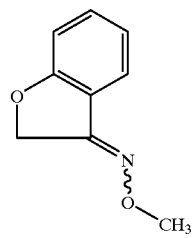

6.7 g (0.05 mol) of benzofuran-3-one are boiled under reflux with 4.2 g (0.05 mol) of O-methylhydroxylamine hydrochloride and 4.1 g (0.05 mol) of sodium acetate in 50 ml of methanol for 3 hours. The solvent is distilled off in vacuo and the reaction mixture is poured onto water and extracted with ethyl acetate. The organic phase is washed with saturated aqueous sodium carbonate solution. The organic phase is dried over sodium sulphate and the solvent is distilled off in vacuo. 7.27 g (89.2% of theory) of crude benzofuran-3-one O-methyl oxime are obtained. For analysis, it is distilled under 2 torr at 70° C. in a bulb tube. An oil is obtained which, both according to the NMR analysis and according to the HPLC analysis, comprises two stereoisomers (79% of isomer B and 21% of isomer A).

2nd Stage

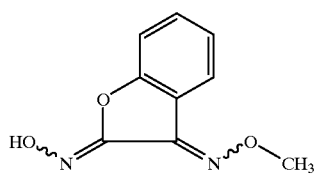

2 g (0.019 mol) of tert-butylnitrite are added dropwise to 30 ml of ethyl acetate saturated with dry hydrogen chloride at −10° C. and the mixture is stirred at this temperature for 15 minutes. 1.6 g (0.0098 mol) of benzofuran-3-one O-methyl oxime dissolved in 5 ml of ethyl acetate are then added at −10° C., the temperature is allowed to rise to 0° C. and the mixture is stirred at this temperature for 30 minutes. The product which has crystallized out is filtered off and 1.08 g of crystalline benzofuran-2,3-dione 3-(O-methyl oxime) 2-oxime are obtained as mixture of two stereoisomers which, according to the HPLC analysis, comprises isomer B to the extent of 54.7% (56% of theory) and isomer A to the extent of 42.9%.

$^1$H-NMR spectrum (CDCl$_3$/TMS): δ=4.10 (3H, isomer B); 4.11 (3H, isomer A); 7.21–7.26 (1H); 7.31–7.35 (1H); 7.5–7.65 (2H, isomer B+1H, isomer A); 8.02–8.05 (1H, isomer A); 11.36 (1H, isomer A); 11.75 (1H, isomer B) ppm.

3rd Stage:

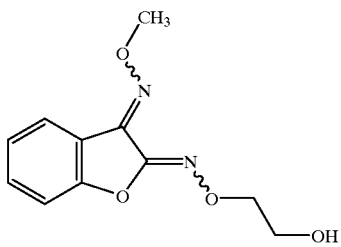

264.3 g (6.0 mol) of ethylene oxide are passed into a solution of 192.2 g (1.0 mol) of benzofuran-2,3-dione 3-(O-methyl oxime) 2-oxime in 2 l of water at 20° C. in the course of 85 minutes. The solution is cooled to 5° C. and 70 g (1.06 mol) of potassium hydroxide lozenges are added, the temperature rising to 10° C. The mixture is stirred for a further 165 minutes without further cooling and the precipitate formed is filtered off with suction, washed with 500 ml of ice-water in portions and dried in a vacuum drying cabinet at 40° C. 143.0 g (61% of theory) of benzofuran-2,3-dione 2-[O-(2hydroxy-ethyl) oxime]-3-(O-methyl oxime) are obtained as a mixture of two stereoisomers.

HPLC: logP=1.65 (0.5%); 1.79 (99.5%)

4th Stage:

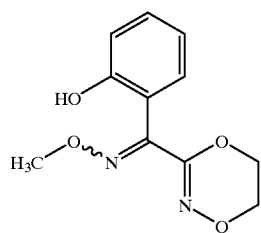

A solution of 25.6 g (0.1084 mol) of benzofuran-2,3-dione 2-[O-(2-hydroxy-ethyl)oxime]3-(O-methyl oxime) and 14.2 g (0.216 mol) of potassium hydroxide lozenges in 250 ml of water is stirred at 60° C. for 195 minutes. The solution is cooled to 10° C. and acidified to a pH of 5–6 with glacial acetic acid. The product which has crystallized out is filtered off with suction, washed with 200 ml of water in portions and dried at 45° C. in a vacuum drying cabinet. 17.7 g (67.7% of theory) of E-(5,6-dihydro-[1,4,2]dioxazin-3-yl)-(2-hydroxy-phenyl)-methanone O-methyl oxime are obtained.

HPLC: logP=1.22

The logP values were determined in accordance with EEC Directive 79/831 Annex V. A8 by HPLC (gradient method, acetonitrile/0.1% strength aqueous phosphoric acid)

What is claimed is:

1. A process for the preparation of compounds of the formula (I)

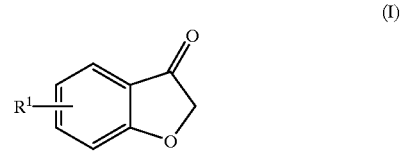

in which

R$^1$ represents hydrogen, alkyl or halogen, comprising reacting salicylic acid ethers of the general formula (II)

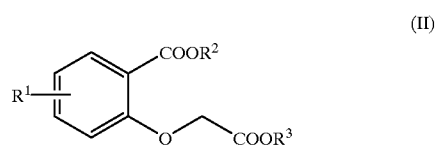

in which

R$^1$ has the abovementioned meaning and

R$^2$ and R$^3$ are identical or different and independently of one another represent alkyl, in a first step with a strong base, optionally under an inert gas atmosphere and/or in the presence of a diluent, and reacting the benzofuranonecarboxylic acid ester obtained in this manner, of the formula (III)

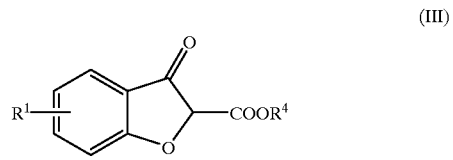

in which

R$^1$ has the abovementioned meaning and

R$^4$ represents alkyl, in a second step first with potassium hydroxide, optionally in the presence of a diluent, and then with an acid to give the desired benzofuranones of the formula (I).

2. The process according to claim 1, characterized in that compounds of the formula (I) in which R$^1$ represents hydrogen, alkyl having 1 to 4 carbon atoms, fluorine or chlorine are prepared.

3. The process according to claim 1, characterized in that compounds of the formula (I) in which $R^1$ represents hydrogen, methyl, ethyl, fluorine or chlorine are prepared.

4. The process according to claim 1, characterized in that alkaline earth metal or alkali metal hydrides or alcoholates are employed as the base.

5. The process according to claim 1, characterized in that the process in the first stage is carried out at temperatures from 0° C. to 150° C.

6. The process according to claim 1, characterized in that the process in the second stage is carried out at temperatures from 0° C. to 150° C.

7. The process according to claim 1, characterized in that in general 0.5 to 10 mol of base are employed per mole of the salicylic acid ether of the formula (II).

8. The process according to claim 1, characterized in that hydrochloric acid, sulphuric acid or phosphoric acid are employed in the second stage of the process.

9. The process of claim 1, characterized in that in general 1 to 10 mol of potassium hydroxide are employed per mole of benzofuranonecarboxylic acid ester of the formula (III).

* * * * *